(12) United States Patent
Park

(10) Patent No.: US 6,475,193 B1
(45) Date of Patent: Nov. 5, 2002

(54) CONTINUOUS INJECTING APPARATUS

(76) Inventor: Ji Hoon Park, Two Fl. 111o, #513 Koduk-dong, Kangdong-gu, Seoul 134-080 (KR)

( * ) Notice: Subject to any disclaimer, the term of this patent is extended or adjusted under 35 U.S.C. 154(b) by 0 days.

(21) Appl. No.: 09/402,271

(22) PCT Filed: Mar. 30, 1998

(86) PCT No.: PCT/KR98/00070

§ 371 (c)(1),
(2), (4) Date: Sep. 29, 1999

(87) PCT Pub. No.: WO98/43690

PCT Pub. Date: Oct. 8, 1998

(30) Foreign Application Priority Data

Mar. 29, 1997 (KR) ............................................ 97-11497
Apr. 25, 1997 (KR) ............................................ 97-15519

(51) Int. Cl.[7] ................................................ A61M 5/00

(52) U.S. Cl. ...................... 604/191; 604/236; 606/116; 81/9.22

(58) Field of Search ................................ 604/181–183, 604/187, 191, 199, 213, 218, 236–238, 247, 257, 131, 151, 57, 59, 60–61, 63, 189; 606/116, 117, 186, 167; 81/9.22

(56) References Cited

U.S. PATENT DOCUMENTS

| 3,353,537 | A | | 11/1967 | Knox et al. |
| 4,594,073 | A | * | 6/1986 | Stine |
| 4,838,866 | A | * | 6/1989 | Marshall, Sr. |
| 5,368,578 | A | * | 11/1994 | Covington et al. |
| 5,520,658 | A | * | 5/1996 | Holm |
| 5,899,885 | A | * | 5/1999 | Reilly et al. |

FOREIGN PATENT DOCUMENTS

GB           1595204           7/1977

* cited by examiner

Primary Examiner—Anhtuan T. Nguyen
Assistant Examiner—LoAn H. Thanh

(57) ABSTRACT

A continuous injecting apparatus comprises an hollow housing (10) including an upper portion and a lower portion (10',10"); a syringe (1) mounted in the hollow housing (10); a connector (20) tightly threaded onto the front end portion of the housing (10); an adjusting portion (90) including an adaptor (50) coupled to the rear end of the hollow housing (10); a plug (60) inserted into the adaptor (50); a plunger (70) including a gripper (74) coupled at the front end to the pushing portion (3b) of the syringe (1), a grasping portion (76) formed to force a user to push down the piston (3) of the syringe (1) and a stopper (80) movably mounted onto a rod of the plunger (70), thereby adjusting an amount of medical liquid to be injected for diagnostic or therapeutic purposes.

26 Claims, 9 Drawing Sheets

CONTINUOUS INJECTING APPARATUS

TECHNICAL FIELD

The invention is related to providing a continuous injecting apparatus for getting a disposal syringe mounted therein to inject medical liquid in a dose to domestic animals such as poultry, horses, pigs, cows, etc., continuously, and then apply the injection mark on the backs or other portions thereof.

BACKGROUND ART

Generally, a syringe is used to inject medical liquid or fluids to human or domestic animals for diagnostic or therapeutic purposes to treat or prevent their diseases. Especially, there are syringes of two types for domestic animals; one is a disposal syringe and other is a continuous throwing-in injector or syringe, which needs its sterilization after being used.

Referring to FIG. 1A, a disposal syringe is shown in a cross-sectional view. The syringe comprises a hollow body 2 including a projecting portion 2a formed on the front end and a flange 2b extended from around the circumference of the rear end, a piston 3 including a head 3a being snugly slidable in the hollow body 2 and a rod 3b being pushed-pulled by a user and a hollow needle 4 fitted onto the projecting portion 2a.

The disposal syringe is very simple in its configuration for one use, but the continuous injecting work for many domestic animals is not possible. Further, it is inconvenient not only to inject a predetermined dose of medical liquid but also to file fluids up in the hollow body.

Referring to FIG. 1B, a conventional continuous injecting apparatus is shown in a cross-sectional view. The continuous injecting apparatus comprises a hollow case 6 including a projecting portion 6a connected at the front end thereof to a hose 9 for supplying medical liquid and a handle portion 6b extended from around the circumference of the rear end, a hollow needle 5 fitted onto the projecting portion 6a, a piston 7 including a head 7a formed at the frond end to be snugly slidable in the hollow case 2 and a pushing portion 7b formed at the rear end to be pushed by a user, a plug 8 thread into the inner portion of the hollow case 6 and for guiding the piston 7 in a longitudinal direction and a spring 10 mounted between the plug 8 and the pushing portion 7b to return the piston 7 to the original position after injecting medical liquid.

The continuous injecting apparatus enables medical liquid to be continuously supplied into the hollow case 6 through the hose 9. Thus, the hollow case 6 can be kept at a full state at the time of the inoculation of domestic animals It means the removal of the disadvantage happened to the disposal syringe and the shortening of the inoculation time.

Nevertheless, it is not possible to inject or inoculate many domestic animals with an amount of medical liquid or virus by using the continuous injecting apparatus. It is anxious that the injection of too much doses due to the unskillfulness of a user may occur the unanticipated things. It is noted that the injection of medical liquid for domestic animals should be continuously done in a dose.

The continuous injecting apparatus requires the disinfection, sterilization or cleaning of its important parts before and/or after the use, which are inconvenient things for a user. The homage or failure of parts may happen during dipping in boiled water for sterilization.

The disposal syringe and the continuous injecting apparatus are not provided with a separated marker. Identifying it on whether the domestic animal in a herd is inoculated is difficult.

An object of the invention is to provide a continuous injecting apparatus including a disposal syringe mounted therein to inject medical liquid in a dose to domestic animals, continuously.

The other object of the invention is to provide a continuous injecting apparatus for enabling a disposal syringe to be easily and removably mounted therein, thereby removing the sterilization, cleaning or disinfection thereof.

Another object of the invention is to provide a continuous injecting apparatus including a adjusting portion for adjusting an amount of medical liquid, thereby enabling an exact dose to be injected.

Another object of the invention is to provide a continuous injecting apparatus including a connector for supplying an amount of medical liquid from outside to a disposal syringe, continuously.

Another object of the invention is to provide a continuous injecting apparatus including a marker mounted thereon to easily determine on whether any domestic animal is injected or inoculated in a group.

DISCLOSURE OF INVENTION

According to the invention, a continuous injecting apparatus comprises an hollow housing including an upper portion and a lower portion; a syringe mounted in the hollow housing; a connector tightly threaded onto the front end portion of the housing and including a needle fitting portion onto which a needle is positioned; an adjusting portion including an adaptor coupled to the rear end of the hollow housing, on the outer circumference of which a handle portion is formed; a plug inserted into the adaptor and including a flange formed to wrap the upper surrounding portion of the adaptor to be coupled thereto; and a plunger including a gripper coupled at the front end to the pushing portion of the syringe, a grasping portion formed to force a user to push down the piston of the syringe and a stopper movably mounted onto a rod of the plunger to adjust an amount of medical liquid to be injected for diagnostic or therapeutic purposes and for supporting a spring with the grasping portion.

According to the other feature of the invention, the continuous injecting apparatus further comprises a marking means mounted on the side portion and the grasping portion to jet an erasable or water soluble paint or give a color indication to domestic animals, in which the marking means comprises a storage for storing a color soluble paint therein, a supply including a first cylinder, in which an inlet port is formed to introduce the paint into the first cylinder and an outlet port is formed to discharge the paint into a chamber, and the chamber for temporally storing the paint; a pump mounted on the chamber to generate the negative pressure; and a jetting portion including a second cylinder, on the front surface of which a second inlet port is formed to introduce the paint therein and on the rear surface of which a plurality of through holes are formed to discharge the paint outside, and a cap including a jetting hole to jet the paint to domestic animals.

According to another feature of the invention, the continuous injecting apparatus furthermore comprises a marking means mounted on a handle portion thereof, in which the marking means includes a storage for storing the color soluble paint therein, a pump mounted to generate the negative pressure in a chamber, a supply including a first cylinder to supply the paint to a second cylinder according to the operation of the pump and a jetting portion including a second cylinder to jet the paint to domestic animals.

BRIEF DESCRIPTION OF DRAWINGS

The invention now will be described in detail with reference to the accompanying drawings, in which.

DETAILED DESCRIPTION OF THE INVENTION

A continuous injecting apparatus comprises a disposal syringe 1, a hollowing housing 10 receiving the disposal syringe 1, a connector 20 for continuously supplying medical liquid to be injected and an adjusting portion for continuously injecting supplied medical liquid to domestic animals with an amount of dose being adjusted.

Figure 1A:
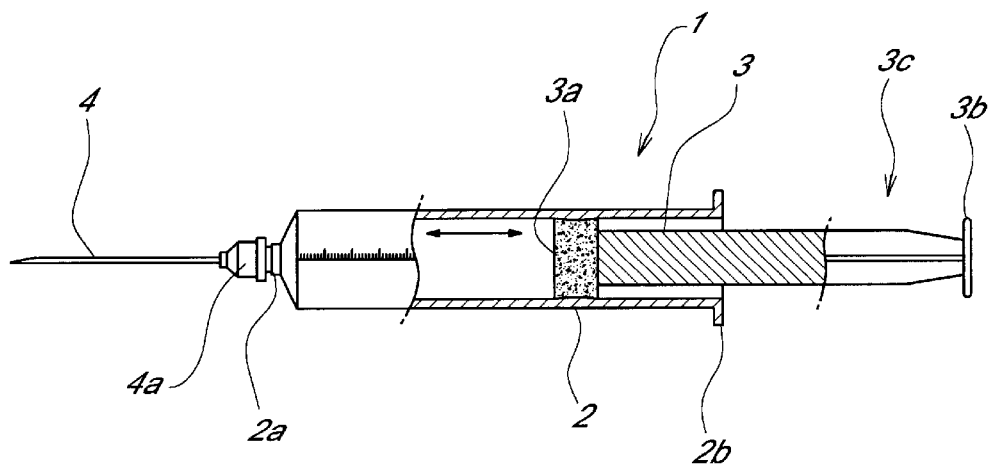
FIGS. 1A and 1B are cross-sectional views illustrating the configuration of a disposal syringe and a conventional continuous injecting apparatus.
Figure 1B:
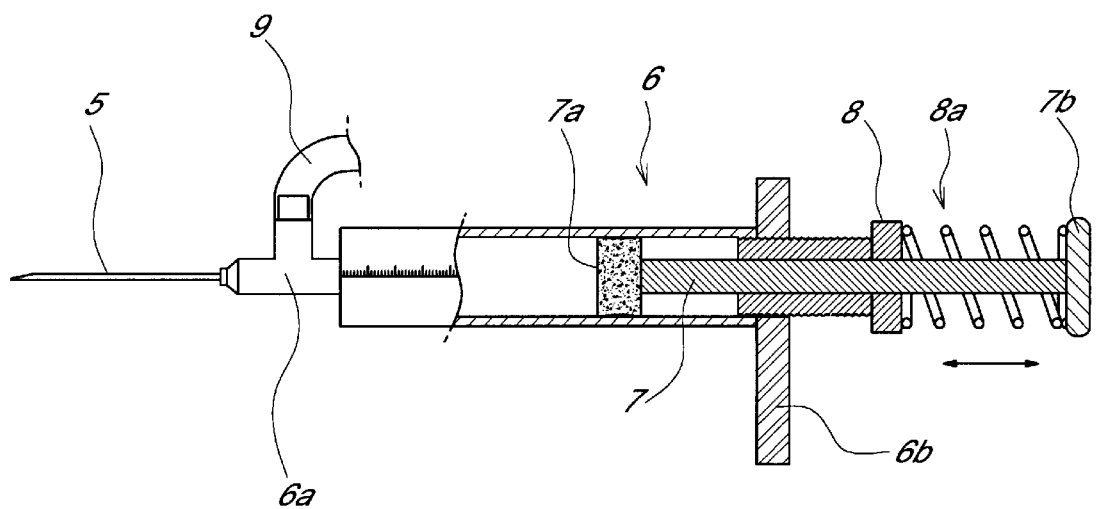

The disposal syringe is the same as that of FIG. 1A, the parts of which are given the same reference number. Herein, the detailed description is omitted.

Figure 2:
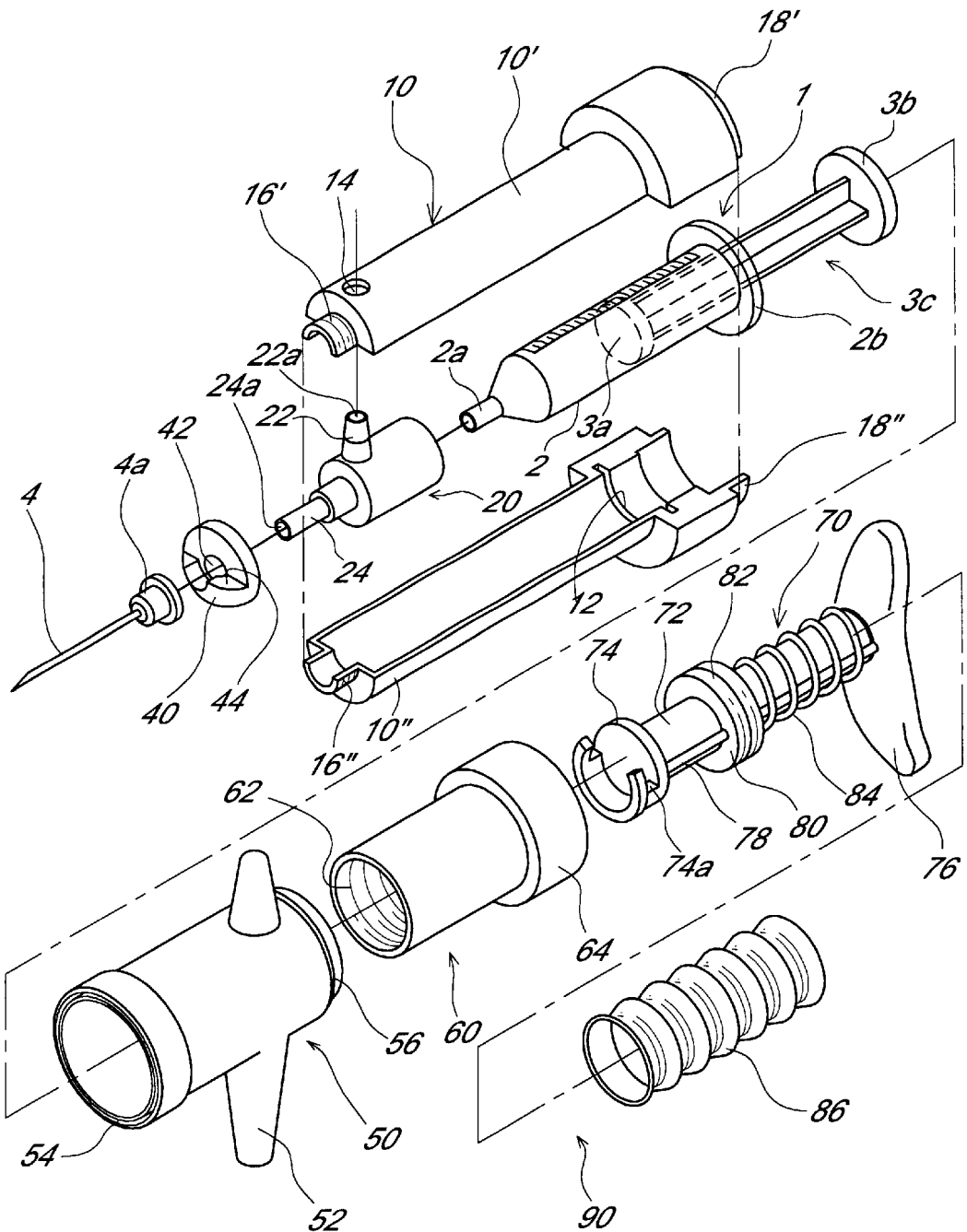
FIG. 2 is an exploded perspective view illustrating a continuous injecting apparatus according to the invention.
Figure 3:
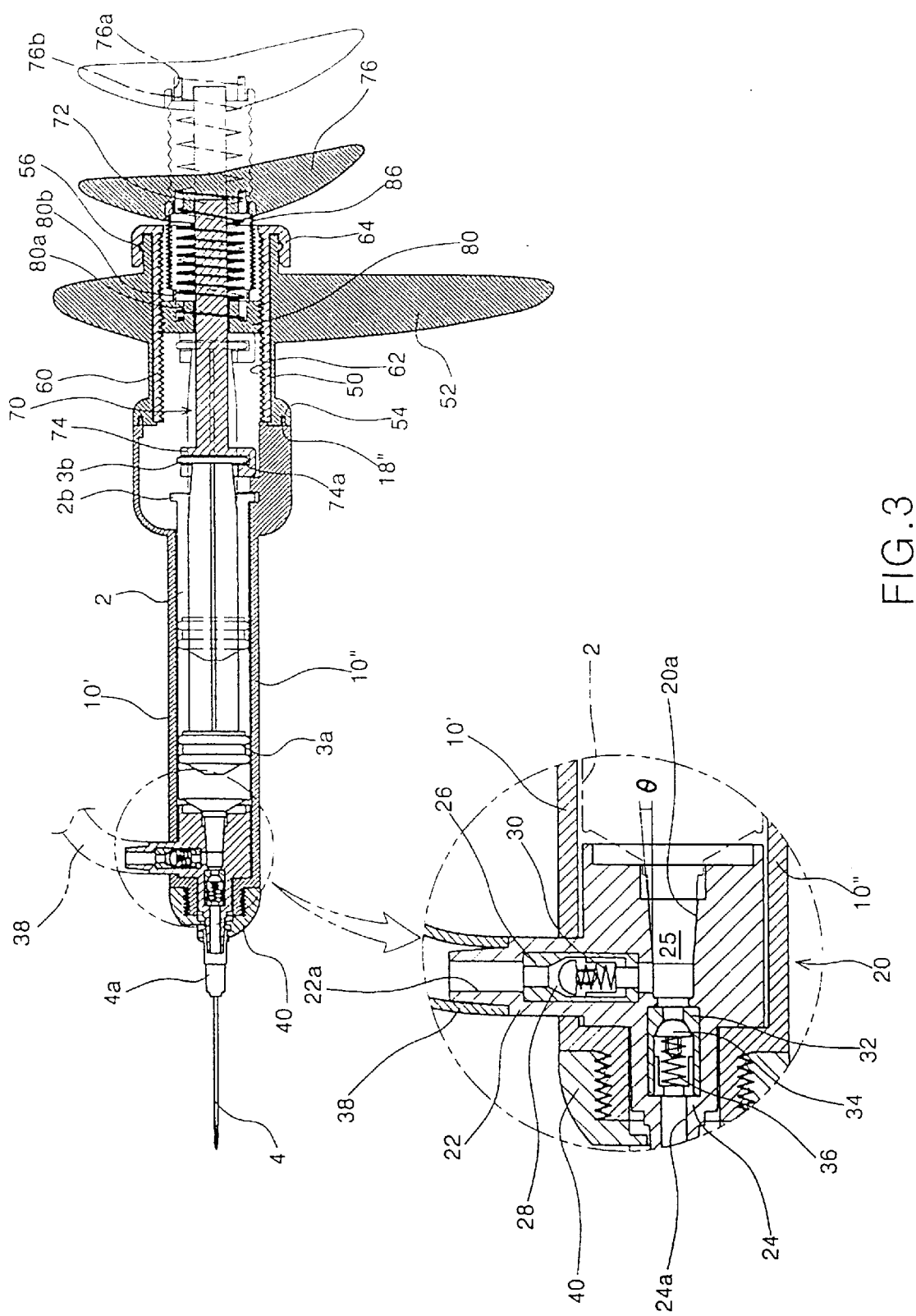
FIG. 3 is a cross-sectional view illustrating the continuous injecting operation of a continuous injecting apparatus according to the principle of the invention.
Figure 4:
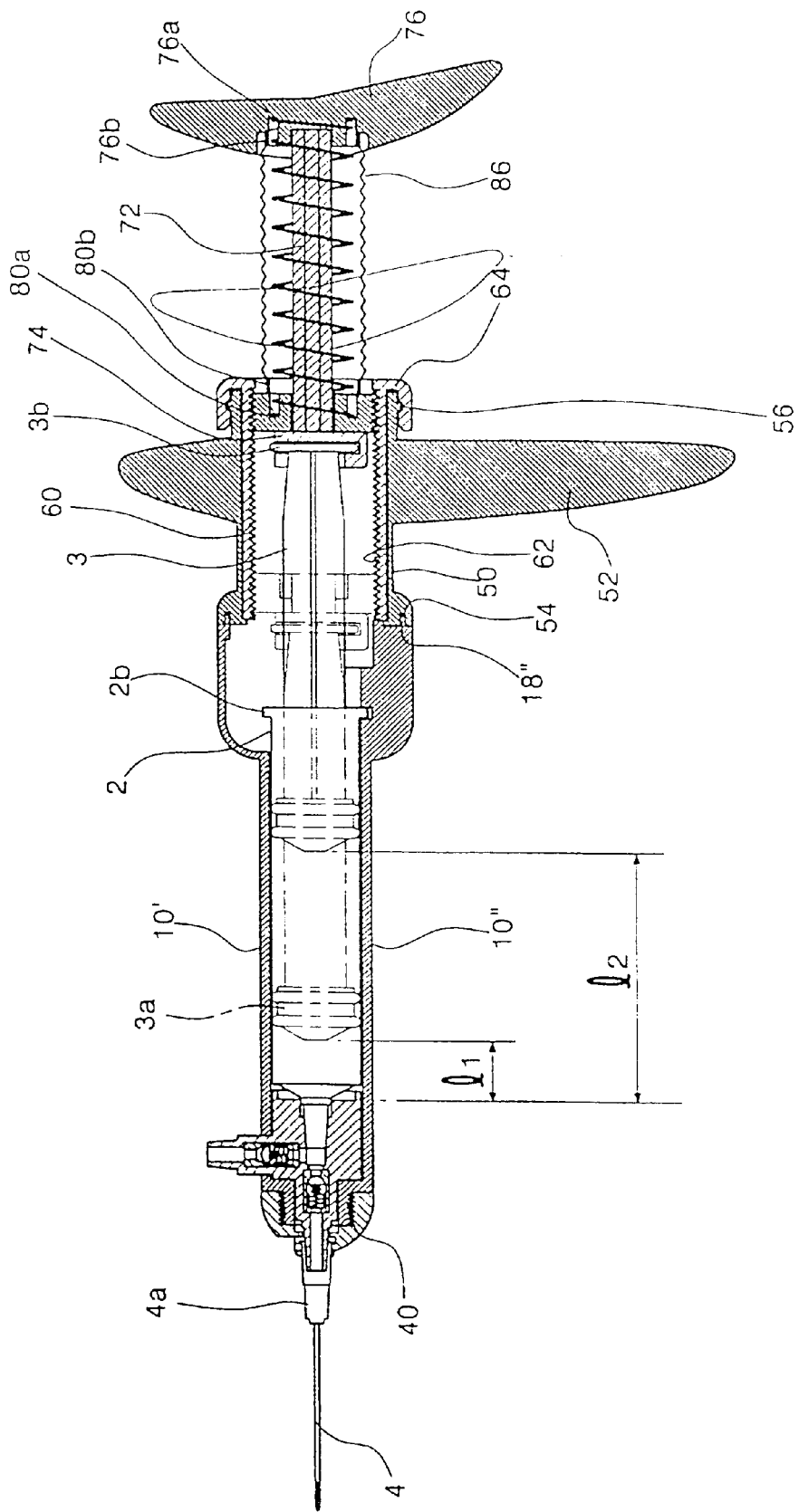
FIG. 4 is a cross-sectional view illustrating the injecting operation of a dose of medical liquid to domestic animals according to the principle of the invention.

Referring to FIGS. 2, 3 and 4, the hollow housing 10 includes an upper portion 10' and a lower portion 10" constituted as a body, in which the upper and lower portions 10' and 10" are in the form of a semi-sphere including threaded portions 16' and 16" formed at the front end portion to be coupled with the clamp 40, grooves 12 formed at the upper and lower portions to receive a flange 2b of the syringe 1 and coupling portions 18' and 18" projected upward from the upper end to be coupled with a coupling groove 54 of the adaptor 50. A medical liquid supplying hole 14 is formed on the upper portion 10' to permit a medical liquid supplying portion 22 to be passed therethrough. The adaptor 50 is integrated with the housing 10. Thus, it is noted that the syringe 1 and the connector 20 are seated in the housing 10.

The connector 20 includes a needle fitting portion 24 and medical liquid supplying portion 22 integrated with each other and a clamp 40 coupled to the needle fitting portion 24 passing through a hole 42 formed at its center. The medical liquid injecting portion 22 includes a hose 38 inserted onto the outer circumference to supply medical liquid from an outer medical bottle (not shown) to the syringe 1. The clamp 40 includes the hole 42 formed at the center to pass the needle fitting portion 24a and a groove 42 receiving a flange 4a of a needle 4 to be fixed to the needle fitting portion 24.

As shown in FIG. 3, the connector 20 includes a first check valve 28 mounted in an inlet port 24a of the medical liquid injecting portion 22 to enable medical liquid to be introduced therein and supply it to the syringe 1, a second valve 34 mounted in an outlet port 24a of the needle fitting portion 24 for enabling medical liquid to be injected to domestic animals and a hollow portion 25 formed around two check valves 28 and 34 and the tip portion of the syringe 1. Also the connector 20 has an inner surface portion 20a enlarged/slanted by an angle θ from the middle of the hollow portion 25 to force a needle fitting portion 2a to be fitted thereinto. The first check valve 28 is arranged to prevent the reverse flow of medical liquid introduced a spring 30. The second check valve 34 is arranged in a rectangular angle to the first check valve 28 to prevent the inflow of air through the outlet port 24a by a spring 36. When the connector 20 is assembled with the housing 10 receiving the syringe 1, the inner rear portion of the connector 20 is coupled onto the threaded portions 16' and 16" and then the clamp 40 is inserted onto the front end of the connector 20.

The adjusting portion 90 comprises an adaptor 50 covering the moving distance of the syringe rod 3, a plug 60 fitted into the adaptor to guide the longitudinal movement of a rod 72 and a plunger 70. The adaptor 50 includes the coupling groove 54 formed in a thickness of the lower portion to be integrated with the coupling portions 18' and 18", a handle portion 52 projected from the upper surface of both sides thereof and a projector 56 formed around the outer circumference to couple with the plug 60. The plug 60 includes a threaded portion 62 formed therein and a receptacle 64 inserted onto the projector 56 to couple with the adaptor 50, in which the receptacle 64 is bent in a distance from the upper end to wrap the upper portion of the adaptor 50. The plunger 70 includes a gripper 74 coupled with the pushing portion 3b of the syringe 1, a grasping portion 76 pushed by a user, a rod 72 forming the length portion between the gripper 74 and the grasping portion 76 and a stopper 80 inserted into the rod 72. The length portion of the rod 72 is somewhat longer than that of the adaptor 50 to be projected from the front end thereof. Key grooves 78 are formed on both sides of the rod 72 to move the stopper 80 upward and downward on the length portion, but not to be rotated on the rod 72. The gripper 74 includes a groove 74 which the pushing portion 3b is seated into to prevent the escape of the syringe 1 during the movement of the piston 3. The stopper 80 includes a threaded portion 82 formed around the outer surface to engage with the threaded portion 62 of the plug 60. A spring 84 is mounted between the stopper 80 and the grasping portion 76 to be returned to the original position after pushing the plunger 70, one end of which is fixed to a projector 80a of the stopper 80 and the other end of which is hooked in a groove 76a of the grasping portion 76. Similarly, a bellows 86 is inserted between the stopper 80 and the grasping portion 76 to prevent the inflow of alien materials outside, one end of which is fixed to a projector 80b and the other end of which is hooked in a groove 76b of the grasping portion 76. Thus, the adjusting portion 90 is assembled in a manner that the plug 50 is mounted into the adaptor 50 by coupling the projector 56 with a groove of the receptacle 64. Then, the plunger 70 is inserted into the plug 60 and positioned at a predetermined place by the stopper 80 with the bellows 86 being arranged between the stopper 80 and the grasping portion 76.

The continuous injecting apparatus is assembled as follows; the disposal syringe 1 is fitted into the rear portion of the connector 20 to receive the needle fitting portion 2a. The flange 3b is seated in the groove 52, while the grasping portion 76 is pushed down with the handle portion 52 being caught by the handle. At that time, the cramp 74 is gone out/projected outer according to the guide of the plug 60, so that the pushing portion 3b is coupled with the groove 74a. Then, the housing 10 is fixed at the projectors 18' and 18" of the rear end to the coupling groove 54 by an adhesive agent or other methods. The needle 4 is assembled by seating the needle fitting portion 4a in the needle fitting groove 44 and then the connector 20 is threadedly coupled with the threaded portions 16' and 16".

In order to use the continuous injecting apparatus, as the plunger 70 is pushed with the grasping portion 76 and the handle portion 52 being held, the piston 3 is slidably moved along the inner surface of the body 2 and air in the body is discharged. When the piston 3 is contacted with the inner front surface of the body 2 by the continuous pushing, the grasping 76 is released from the pushing force to be free and then retracted to generate the negative pressure. At that time, the negative pressure is greater than that of the spring 30. It forces the first check valve 28 to be operated so that the inlet port 22a is opened to inflow medical liquid from the hose 38 into the body 2. As the piston 3 is moved backward to the original position as shown in a dot line, the body 2 is filled up by medical liquid. While the first check valve 28 closes the inlet port 22a due to the disappearance of the negative pressure. Next, as the grasping portion 76 is pushed, the piston 3 is moved to press medical liquid introduced. At that time, the second check valve 34 pushes against the spring 36 to open the outlet port 24a. At that time, medical liquid discharged is injected to domestic animals.

It is noted that the invention can inject medical liquid to domestic animals, continuously, unless the supply of medical liquid is performed through the hose 38 Also, the invention can inject medical liquid at an amount of dose to domestic animals.

As shown in FIG. 4, the principle of the invention is illustrated in a cross-sectional view. A stopper 80 is movable up and down along a key groove 78, but not rotated around a rod 72 by itself. Also, an outer threaded portion 82 of the stopper 80 is engaged with an inner threaded portion 62 of a plug 60. Thus, upon the assembly of a continuous injecting apparatus, the stopper 80 is positioned into the plug 60 with being inserted onto the rod 72. As a receptacle 64 of the plug 60 is rotated with the handle portion 52 and the grasping portion 76 being fixed by the hand, simultaneously, the stopper 80 is moved along the rod 80 in the plug 60. For example, as the plug 60 is rotated in any direction, the stopper 80 can be set in any predetermined positioned between the front line and the rear line as shown in a dot line. If the stopper 80 is positioned on the front line, the position that is moved by a piston 3 in a body 2 of a syringe 1 is a stroke $l_1$ set at a minimum amount of medical liquid. A stroke $l_2$ at the most rear line of the piston 3 is set at a maximum amount of medica liquid be injected. Herein, it is noted that the adjustment of medical liquid can be accomplished.

A continuous injecting apparatus further comprises a marker for giving a color indication to domestic animals so that the inoculation is identified a number of examples are shown in FIGS. 5 to 9 with the marker being mounted on a handle portion 52 of the continuous injecting apparatus.

Figure 5:
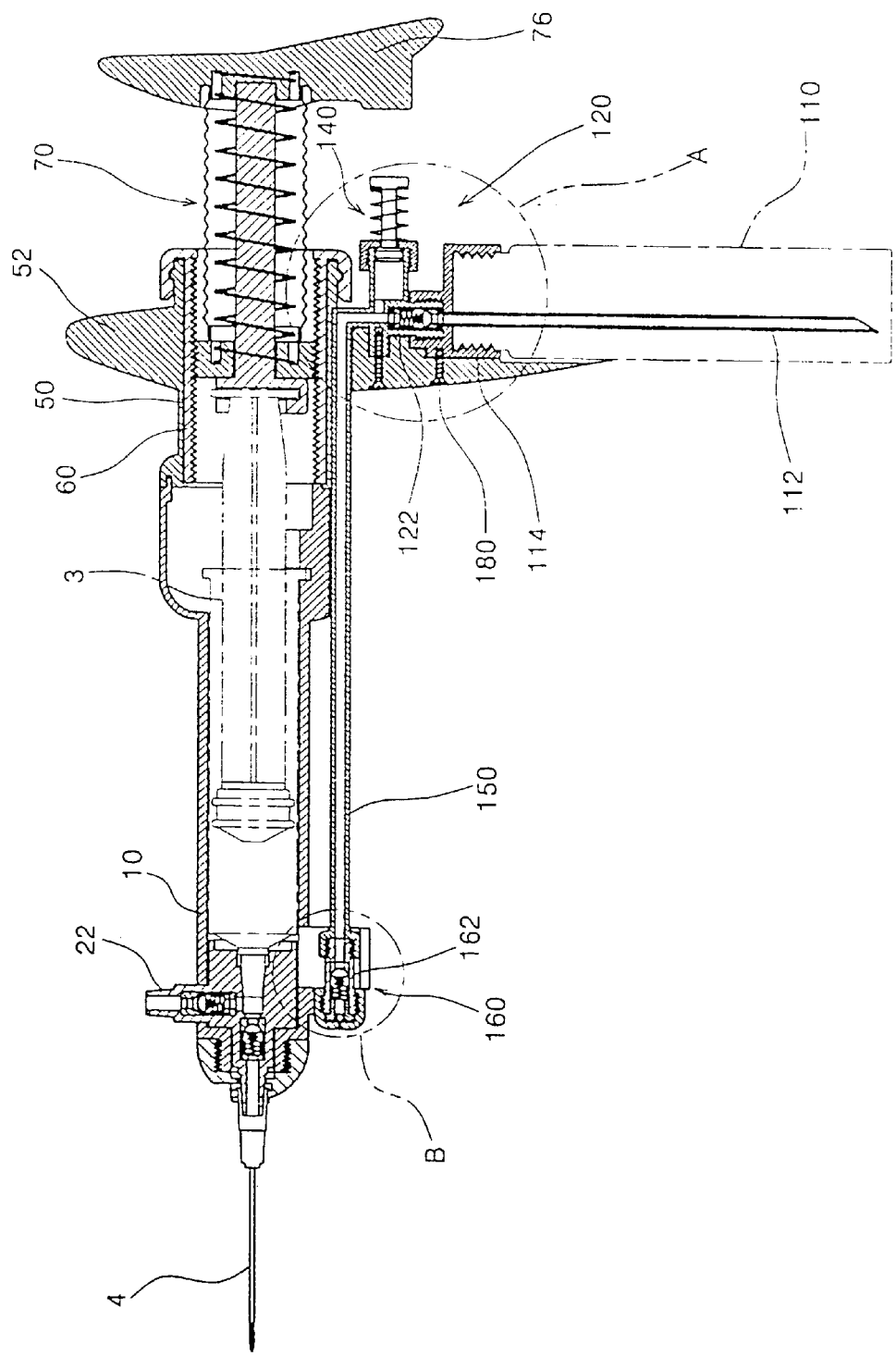
FIG. 5 is a cross-sectional view illustrating the configuration of a continuous injecting apparatus including a marker for jetting water soluble paint to identify the injected domestic animal according to one feature of the invention.
Figure 6A:
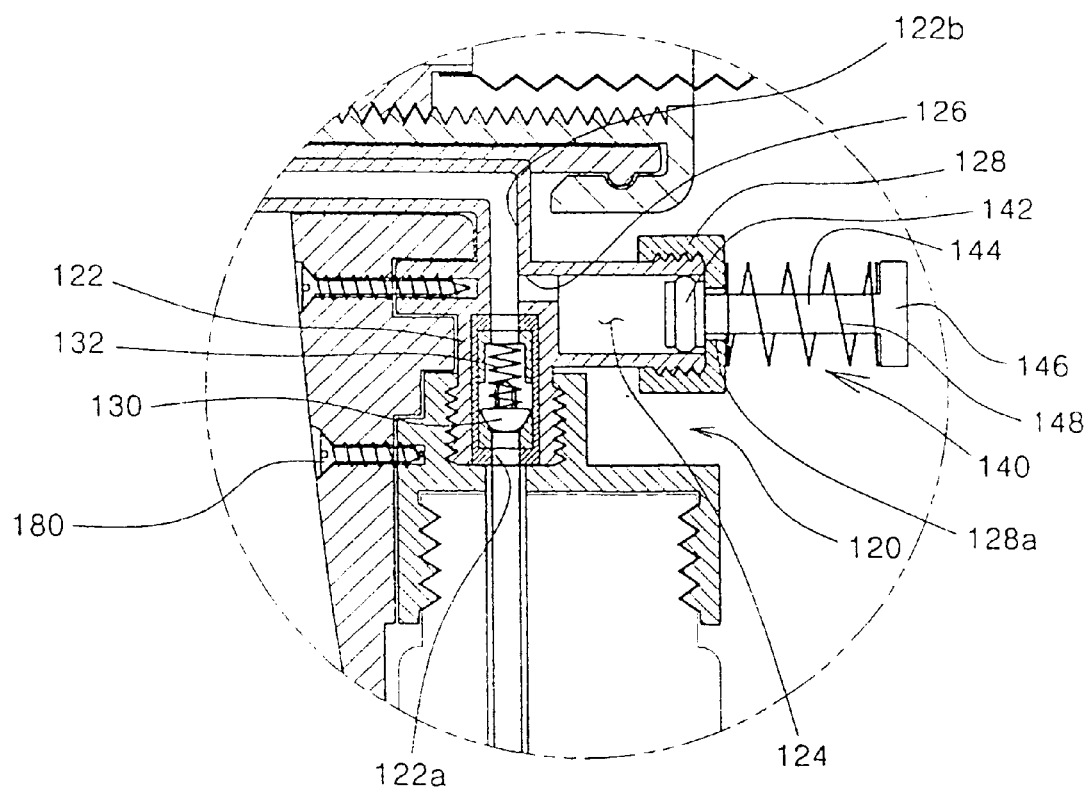
FIGS. 6A and 6B are enlarged cross-sectional views illustrating the jetting portion and supplying portion of the marker of FIG. 5.
Figure 6B:
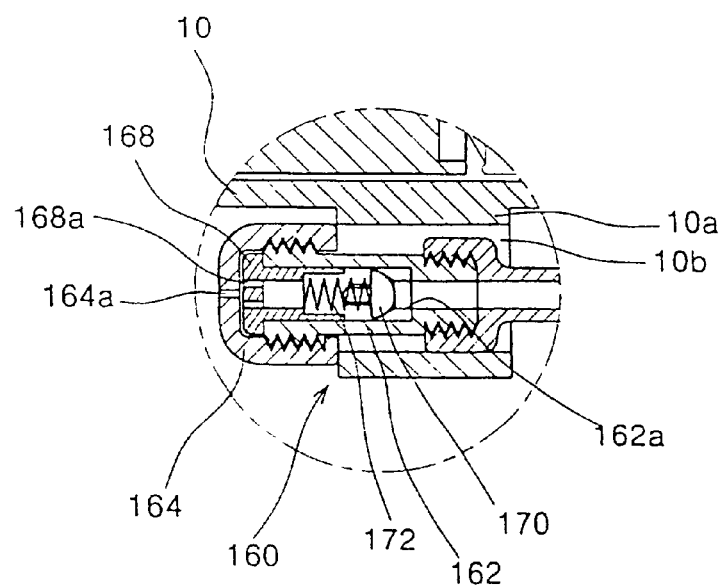

Referring to FIGS. 5, 6A and 6B, the marker comprises a storage 110 for storing a water soluble color paint, a supply 120 including a first cylinder 122 and a chamber 124 for permitting the paint to be introduced therein from the storage 110, storing the paint, temporally and preventing the reverse flow of the paint, a pump 140 for generating the negative pressure in the chamber 124 and a jetting portion 160 including a second cylinder 162 for jetting the paint through a pipe 150 from the chamber 124.

The supply 120 includes a cap member 114 integrated therewith and a straw 112 fixed to the inlet port of the first second valve 122, in which the cap member 114 is coupled with the storage 110 with the straw 112 being inserted. The straw 112 guides the paint in the storage 110 into the cylinder 114 during using.

As shown in FIG. 6A, the first cylinder 122 includes a first inlet port 122a for introducing the paint from the storage 110 therein and a second inlet port 122b guiding the paint into the chamber 124. The first cylinder 122 also includes a first check valve 130 and a spring 132 to permit the paint to be introduced thereinto and prevent the reverse flow of the paint.

The pump 140 is mounted on the chamber 124 to generate the negative pressure. To it, the pump 140 includes a first cap 128 sealing the chamber 124, a piston 142 slidable moved in the chamber 124, a button 146 pressed by a grasping portion 76 and a return spring 148 inserted between the first cap 128 and the button 146, in which the piston 144 includes a rod 146 to be guided by a hole 128a formed on the first cap 128.

As shown in FIG. 6B, the pipe 150 is extended from the supply 120 to the jetting portion 160 passing through a handle portion 52, to the other end of which the jetting portion 160 is attached. The jetting portion 160 is positioned in a hollow portion 10b of a receiving portion 10a which is integrally extended from the housing 10. The injecting portion 160 includes a second cylinder 162 and a second cap 164 threaded to or integrated with the second cylinder 162. The second cylinder 162 is constituted as a second check valve including a second valve 170 and a spring 172 supporting the second valve 170 to permit the paint to be introduced therein through a second inlet port 162a while to discharge it through a second jetting port 164a formed on the second cap 164. A pressure plate 160 is mounted between the second cap 164 and the second cylinder 162 and includes a plurality of through holes 168a aligned with or formed around the jetting port 164a.

The marker is operated as follows; the button 146 is pressed by the grasping portion 76. Air or the paint in the chamber 124 is supplied through the pipe 150 to the second cylinder 163 during the pressing of the button 146. At that time, the first cylinder 122 forces the first valve 30 to close the first inlet port 122a, thereby preventing the reverse flow of the paint into the storage 110.

After the completion of discharging air or supplying the paint, the button 146 is returned along the inner wall of the chamber 124 to the original position by the spring 148 and to generate the negative pressure. At that time, the negative pressure larger than the force of the spring 132 is acted on the first check valve 130. The first cylinder 130 permits the paint to be introduced into the chamber 124 through the inlet port 122a.

Figure 7:
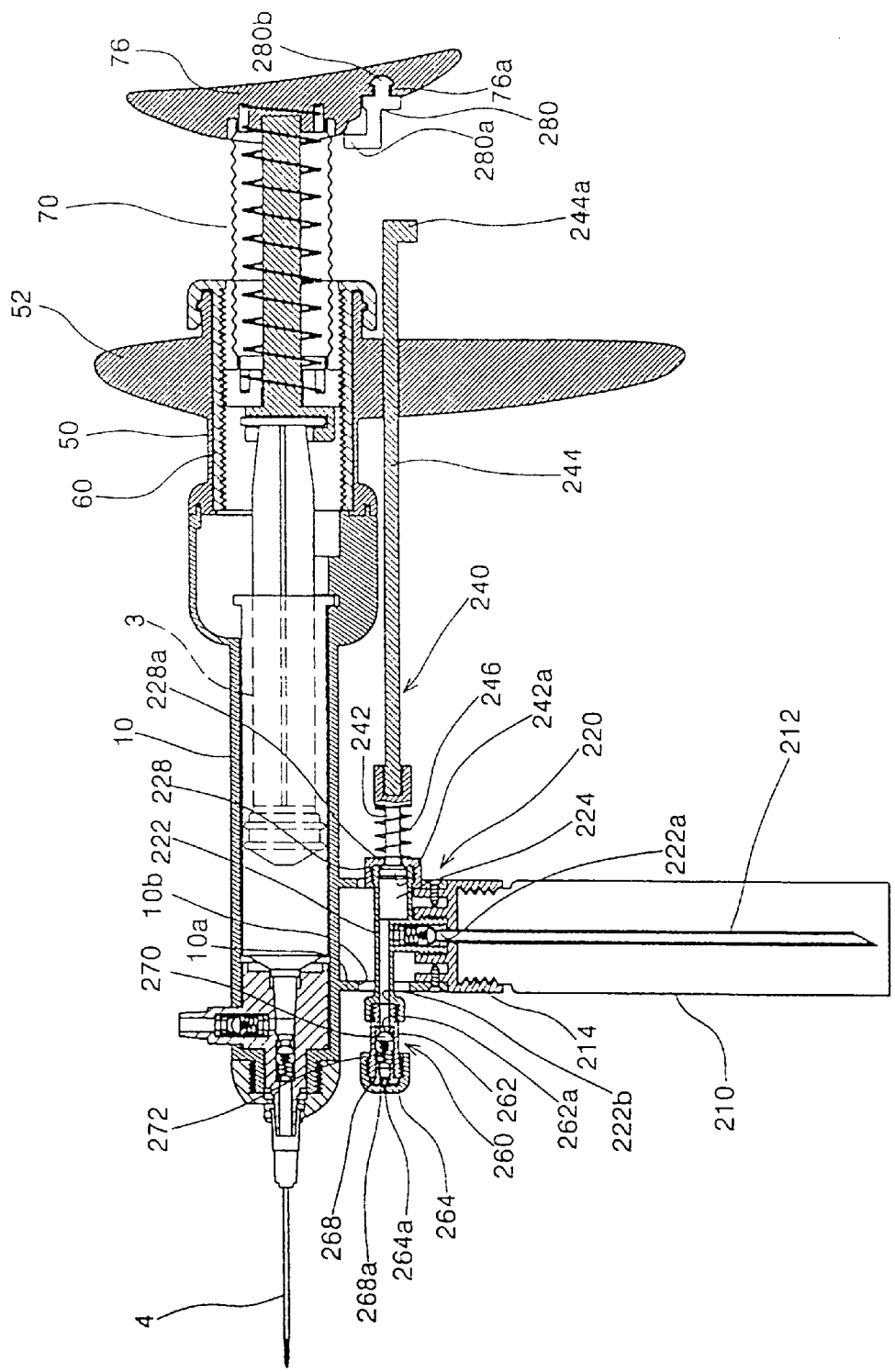
FIG. 7 is a cross-sectional view illustrating the configuration of a continuous injecting apparatus including a marker for jetting water soluble paint to identify the injected domestic animal according to the other feature of the invention.

Referring to FIG. 7, the other embodiment of a marker is shown in a cross-sectional view. The maker is mounted on the side of a housing in a manner that a pump is positioned on the front portion of a continuous injecting apparatus for the purpose of jetting the paint by a stronger force. The marker is similar to the configuration of the first embodiment.

The same parts as those of the first embodiment are referenced by the number adding 100 thereto, the detailed description of which is omitted. A supply 220 is coupled to a jetting portion 260 in a manner that a first cylinder 222 is arranged adjacent to a second cylinder 262 and the a first outlet port 222b is threaded to a second inlet port 262a.

The pump 240 further comprises a first connecting rod 242 and a second connecting rod 244 coupled to each other. The second connecting rod 244 is passed through a handle portion 52, at the end of which a button 244a is formed. A release portion 280 is mounted on the rear portion of a grasping portion 76 in a manner that a rotating portion 280b is rotatably mounted in a groove 76a and a release button 280a is coupled with or separated from the button 244a. Thus, during the use of the marker, the button 244a is coupled with the release button 280a. On the contrary, during the non-use of the marker, the button 244a is separated from the release button 280a not to operate the marker. The operating method of the marker is the same as that of the first embodiment.

Figure 8:
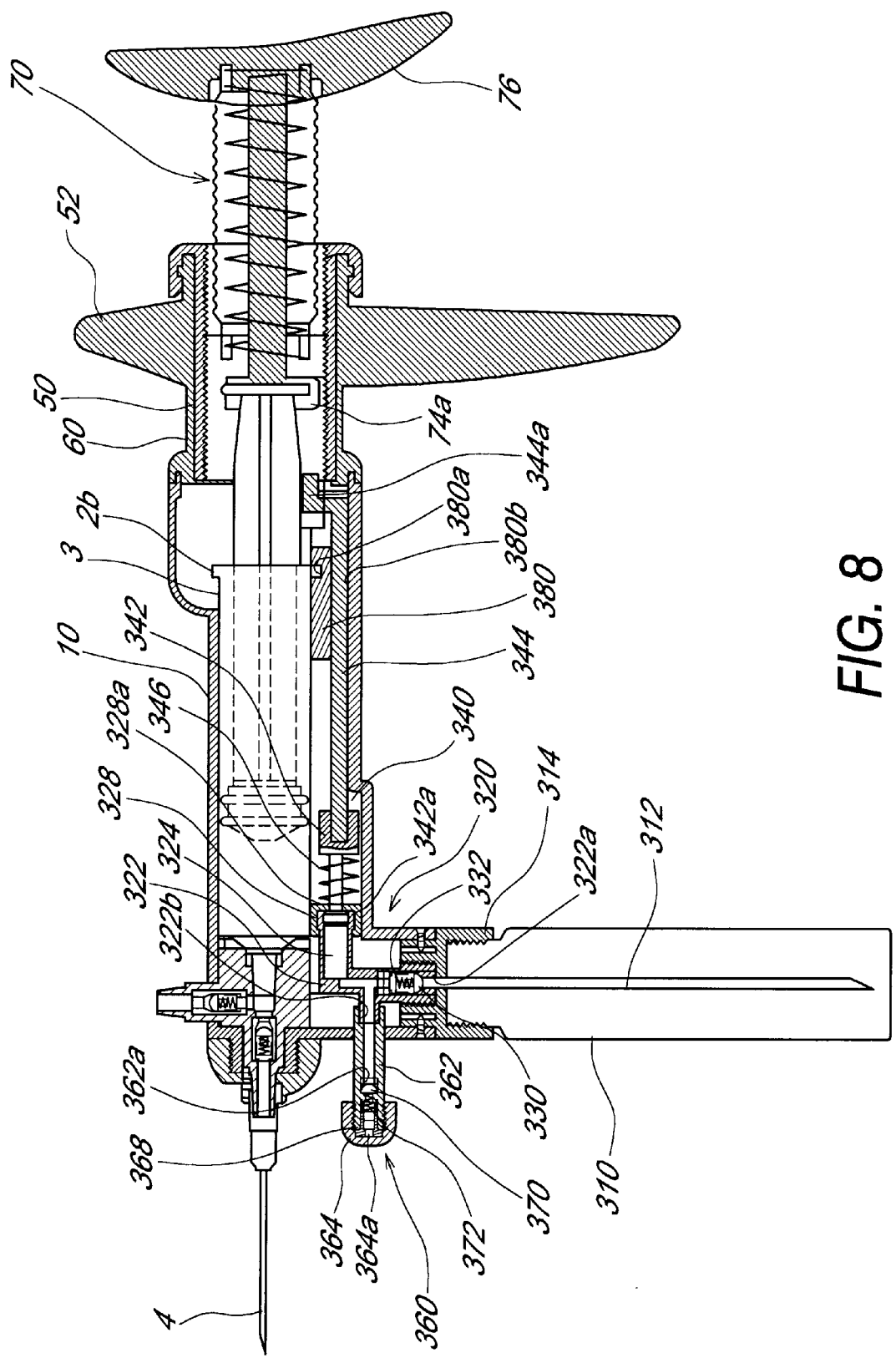
FIG. 8 is a cross-sectional view illustrating the configuration of a continuous injecting apparatus including a marker for jetting water soluble paint to identify the injected domestic animal according to another feature of the invention; and, FIG. 9 is a cross-sectional view illustrating the configuration of a continuous injecting apparatus including a marker for jetting water soluble paint to identify the injected domestic animal according to another feature of the invention.

Referring to FIG. 8, another embodiment of a marker is shown in a cross-sectional view. The maker is mounted in a housing 10 of a continuous injecting apparatus for the purpose of jetting the paint by a stronger force. The same parts as those of the first embodiment are referenced by the number adding 200 or 100 thereto, the detailed description of which is omitted. The marker is configured to force a gripper 74a to press a button 340 instead of a grasping portion 76. For example, A supply 320 is coupled to a jetting portion 360 in a manner that a first cylinder 322 is arranged adjacent to a second cylinder 362 and a first outlet port 322b is threaded to a second inlet port 362a. A chamber 324 is arranged over a second cylinder 360 as shown in the drawing unlike second embodiment that the second cylinder 260 is aligned with the chamber 224.

A pump 340 further comprises a first connecting rod 342 and a second connecting rod 344 coupled to each other. The second connecting rod 344 includes a button 344a formed at the other end to be pressed by a gripper 74a. To it, a spacer 380 is mounted on one inner wall of the housing 10 to permit the second connection rod 344 to be slidable between the housing 10 and the spacer 380. A groove 380a is formed to seat the flange 2b therein. A guide groove 380b is formed to guide the second connecting rod 342 along the lengthwise of the housing 10. The operating method of the marker is the same as that of the second embodiment.

Figure 9:
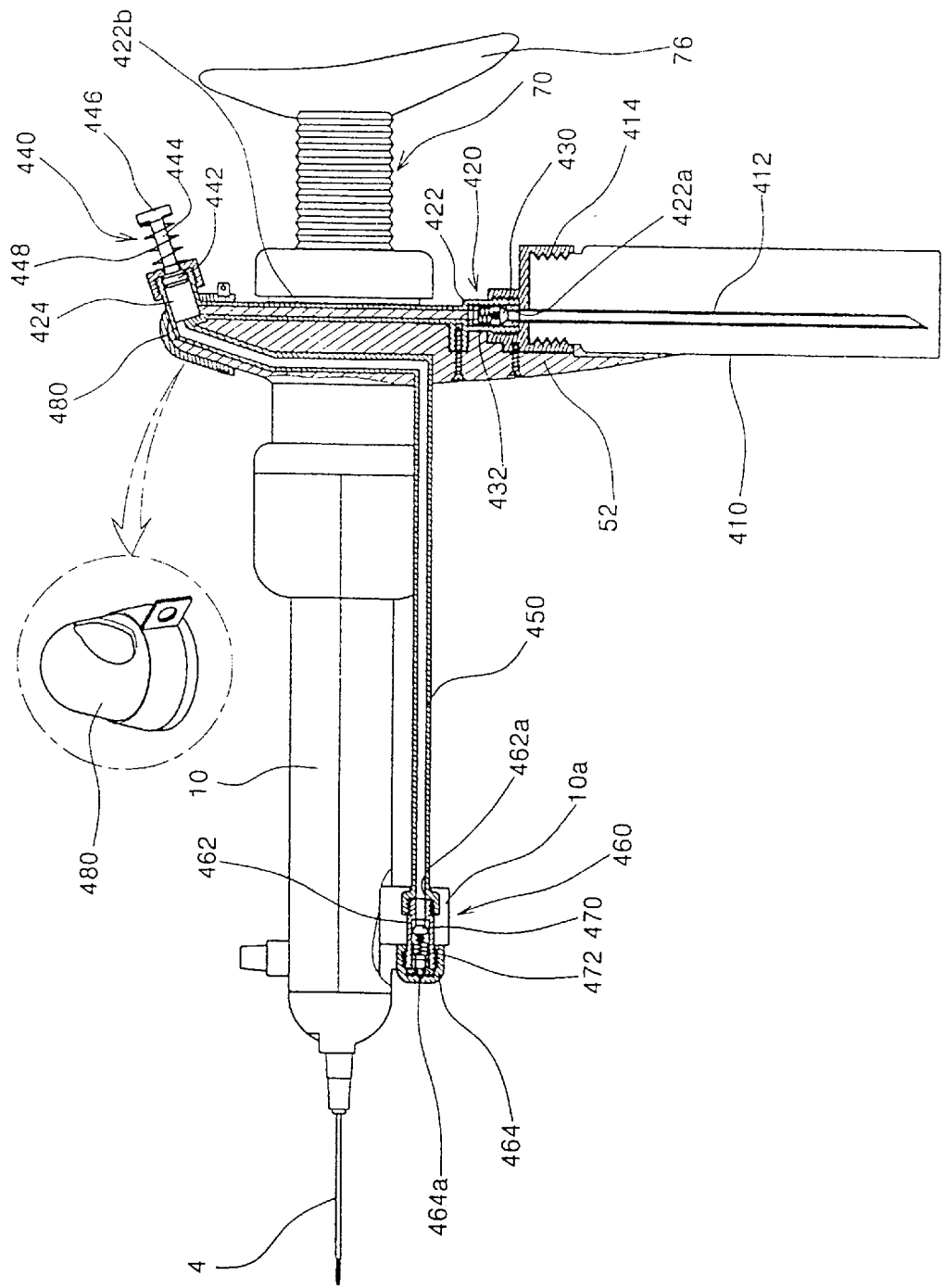

Referring to FIG. 9, still another embodiment of a marker is shown in a cross-sectional view. The maker is mounted on the side wall of a housing in a manner that a pump 440 is position on the upper portion of a handle portion 52. The marker is similar to the configuration of the first embodiment. The same parts as those of the first embodiment are referenced by the number adding 400 thereto, the detailed description of which is omitted.

A storage 110 is mounted on the one upper portion of the handle portion 52 like the first embodiment, and the pump 440 is mounted on the other upper portion of the handle portion 52 by means of a clip 480. A first cylinder 422 is connected by a connection tube 422b to a chamber 424 passing through the handle portion 52. A pipe 450 is mounted between the chamber 424 and a second cylinder 460 passing through the handle portion 52. Thus, the pump 440 is operated to press the button 446 by the hand. The operating method of the marker is the same as that of the first embodiment.

INDUSTRIAL APPLICABILITY

According to the invention, a continuous injecting apparatus can inject medicalliquid in a predetermined amount of dose to domestic animals, continuously. The continuous injecting apparatus facilitates a disposal syringe to be replaced by a new one without the sterilization, disinfection and cleaning. Further, the continuous injecting apparatus is provided with a marker to facilitate a color indication to be performed for domestic animals, thereby identifying on whether any domestic animal is inoculated.

What is claimed is:

1. A continuous injecting apparatus comprising:

a housing having upper and lower portions, the upper and lower portions configured to be separated and adapted to receive a disposable syringe having a piston and a piston rod;

a connector configured to connect the upper and lower portions of the housing; and a pushing assembly coupled to a rear end of the housing and configured to transfer input force to the piston of the disposable syringe, wherein front portions of the upper and lower portions are threadedly engaged with a threaded portion of a clamp.

2. The continuous injecting apparatus of claim 1, wherein the pushing assembly comprises:

an adaptor coupled to a rear end of the housing;

a plug inserted onto the adaptor and including a flange formed to mate with a portion of the adaptor; and a plunger including (1) a gripper adapted to couple to a rear end of the piston rod of the syringe, (2) a grasping portion configured to transfer input force to the piston rod of the syringe and (3) a stopper movably mounted onto a rod of the plunger so as to adjust an amount of fluid to be injected.

3. The continuous injecting apparatus as claimed in claim 2, in which:

a liquid supplying hole is formed on any one of the upper and lower portions.

4. The continuous injecting apparatus of claim 3, wherein the connector comprises a liquid supplying portion configured to supply liquid to the syringe through the liquid supplying hole.

5. The continuous injecting apparatus of claim 4, wherein the connector comprises a first check valve formed on the liquid supplying portion and configured to control the liquid to be introduced therethrough and supply it into the syringe.

6. The continuous injecting apparatus of claim 5, wherein the connector comprises a needle fitting portion configured to allow liquid communication between a syringe needle and the syringe.

7. The continuous injecting apparatus of claim 6, wherein the connector comprises a second check valve formed in the needle fitting portion and configured to control the liquid supplied in the syringe to be injected.

8. The continuous injecting apparatus as claimed in claim 2, in which:

a key groove is formed on both sides of a rod of the plunger to prevent the rotation of the stopper.

9. The continuous injecting apparatus as claimed in claim 2, in which:
the connector includes an inner surface portion enlarged/slanted by an angle θ from the middle of the hollow portion to force a needle fitting portion to be fitted thereinto.

10. The continuous injecting apparatus of claim 2, in which:
a groove is formed on the grasping portion to receive a pushing portion of the syringe.

11. The continuous injecting apparatus of claim 1, further comprising a marking assembly connected to the housing and configured to provide a colored liquid.

12. The continuous injecting apparatus as claimed in claim 11, in which:
the marking assembly includes a storage for storing color soluble paint therein, a pump mounted to generate the negative pressure in a chamber, a supply including a first cylinder to supply the paint to a second cylinder according to the operation of the pump and a jetting portion including a second cylinder to jet the paint to domestic animals.

13. The continuous injecting apparatus as claimed in claim 12, in which:
the supply is coupled to a jetting portion in a manner that the first cylinder is arranged adjacent to the second cylinder and a first outlet port is threaded to a second inlet port, the pump includes a first connecting rod and a second connecting rod coupled to each other, in which the second connecting rod is passed through a handle portion, a button is formed at the end of the second rod.

14. The continuous injecting apparatus as claimed in claim 13, in which:
a release portion is mounted on the rear portion of the grasping portion to be coupled with or separated from the button in a manner.

15. The continuous injecting apparatus as claimed in claim 12, in which:
the supply is coupled to a jetting portion in a manner that the first cylinder is arranged adjacent to the second cylinder and a first outlet port is threaded to a second inlet port, a chamber is arranged over a second cylinder and a pump includes a first connecting rod and a second connecting rod coupled to each other.

16. The continuous injecting apparatus as claimed in claim 12 in which:
a spacer is mounted on one inner wall of the housing to permit the second connection rod to be slided between the housing and the spacer, a groove is formed to seat the flange of the syringe therein to guide the second connecting rod along the lengthwise dimension of the housing.

17. The continuous injecting apparatus as claimed in claim 15, in which:
the first cylinder is connected by a connection tube to a chamber passing through the handle portion, a pipe is mounted between the chamber and the second cylinder of the jetting portion passing through the handle portion and the pump is slided in the chamber by pressing the button by hand.

18. The continuous injecting apparatus as claimed in claim 11, in which:
the marking assembly comprises a storage for storing a color soluble paint therein; a supply including a first cylinder constituted as a check valve, on the front surface of which an inlet port is formed to introduce the paint into the first cylinder and on the rear surface of which an outlet port is formed to discharge the paint into a chamber, and the chamber for temporally storing the paint; a pump mounted on the chamber to generate the negative pressure; and a jetting portion including a second cylinder, on the front surface of which a second inlet port is formed to introduce the paint therein and on the rear surface of which a plurality of through holes are formed to discharge the paint outside, and a cap including a jetting hole to jet the paint to domestic animals.

19. The continuous injecting apparatus as claimed in claim 18, in which:
the pump includes a first cap sealing the chamber, a piston slidable moved in the chamber, a button pressed by a grasping portion and a return spring inserted between the first cap and the button, in which the piston includes a rod to be guided by a hole formed on the first cap.

20. The continuous injecting apparatus as claimed in claim 18, in which:
the first cylinder includes a first valve elastically supported by a spring to open the first inlet port according to the operation of the button.

21. The continuous injecting apparatus as claimed in claim 18, in which:
the second cylinder includes a second valve elastically supported by a spring to open the second inlet port according to the operation of the button.

22. The continuous injecting apparatus as claimed in claim 18, in which:
the first cylinder includes a straw inserted in the storage to supply the paint thereto.

23. The continuous injecting apparatus as claimed in claim 18, in which:
the second cylinder includes a pressure plate on which a plurality of through holes is formed.

24. The continuous injecting apparatus as claimed in claim 18, in which:
the storage is removably coupled to the lower portion of the first cylinder by a cap member.

25. A continuous injecting apparatus with a disposable syringe comprising:
a hollow housing including: a connector coupled to a front portion of the syringe to supply liquid to be injected to the disposal syringe including a syringe rod and a pushing portion, and a clamp coupled to a needle fitting portion of the syringe to allow a needle to be communicated with the syringe positioned therein, wherein the connector and the clamp are assembled in order to form an injection portion; and
an adjusting portion including: an adaptor coupled to a rear end of the hollow housing, which covers the moving distance of the syringe rod, a plug fitted into the adaptor to guide the longitudinal movement of the syringe rod, a plunger coupled to a front end of the pushing portion to operate the syringe and a stopper movably mounted onto a rod of the plunger to adjust an amount of the liquid to be injected, the adaptor, wherein the plug and the plunger are assembled in order to form an operating portion.

26. A continuous injecting apparatus comprising:
a housing having upper and lower portions, the upper and lower portions configured to be separated and adapted to receive a disposable syringe having a piston and a piston rod;

a connector configured to connect the upper and lower portions of the housing; and a pushing assembly coupled to a rear end of the housing and configured to transfer input force to the piston of the disposable syringe, the pushing assembly comprising:

an adaptor coupled to a rear end of the housing;

a plug inserted onto the adaptor and including a flange formed to mate with a portion of the adaptor; and a plunger including (1) a gripper adapted to couple to a rear end of the piston rod of the syringe, (2) a grasping portion configured to transfer input force to the piston rod of the syringe and (3) a stopper movably mounted onto a rod of the plunger so as to adjust an amount of fluid to be injected.

* * * * *